United States Patent [19]

Nelson et al.

[11] Patent Number: 4,883,860
[45] Date of Patent: Nov. 28, 1989

[54] TRIAZINE-BASED LIGHT STABILIZERS FOR PLASTICS

[75] Inventors: Richard V. Nelson, Wilmington, Del.; John F. Stephen, West Chester, Pa.

[73] Assignee: ICI Americas Inc., Wilmington, Del.

[21] Appl. No.: 284,573

[22] Filed: Dec. 15, 1988

[51] Int. Cl.[4] .............................................. C08K 5/34
[52] U.S. Cl. ..................................... 524/98; 524/100; 544/198
[58] Field of Search .................. 524/98, 100; 544/198

[56] References Cited

U.S. PATENT DOCUMENTS

| | | | |
|---|---|---|---|
| 3,488,290 | 1/1970 | Gerhardt et al. | 524/83 |
| 3,489,713 | 1/1970 | Bowman et al. | 524/83 |
| 3,496,134 | 2/1970 | DiGiaimo | 524/83 |
| 3,497,506 | 2/1970 | Traber | 524/83 |
| 3,684,765 | 8/1972 | Matsui et al. | 524/103 |
| 4,348,493 | 9/1982 | Loffelman | 544/198 |
| 4,670,488 | 6/1987 | Maegawa et al. | 524/103 |
| 4,769,443 | 9/1988 | Cantatore | 524/100 |

*Primary Examiner*—John Kight
*Assistant Examiner*—Kriellion S. Morgan
*Attorney, Agent, or Firm*—William E. Dickheiser

[57] ABSTRACT

Triazine-based compounds having a multiplicity of 2,2,6,6-tetraalkyl piperidine moieties are light and thermal stabilizers for organic polymers.

11 Claims, No Drawings

TRIAZINE-BASED LIGHT STABILIZERS FOR PLASTICS

The invention is directed to polymeric compositions which are resistant to degradation and discoloration when exposed to actinic radiation. In particular, it is directed to resins such as polypropylene, polyethylene, etc. which are stabilized with an effective amount of a triazine-based compound which contains the 2,2,6,6-tetraalkylpiperidine moiety. The invention is further directed to a novel group of compounds which are useful as additives for synthetic polymers which act to retard photodegradation.

Many synthetic organic polymers deteriorate rapidly when exposed to sunlight. To circumvent this rapid degradation many additives have been developed to stabilize these resins against the harmful radiation. Among these additives are the UV absorbers such as the hydroxybenzophenones and the hydroxyphenylbenzotriazoles, the organonickel complexes which serve to quench excited states, and most recently the hindered amine light stabilizers (HALS). The HALS possess the 2,2,6,6-tetraalkylpiperidine group that is most commonly substituted in the 4-position and act as radical scavengers, thus inhibiting the degradation process.

Among the requirements for a compound to be an effective light stabilizer are the need for it to be compatible with the resin in which it is to be incorporated, sufficiently nonvolatile so as to remain in the resin during and after processing at elevated temperatures and be resistant to extraction by water. Of the piperidine compounds disclosed to date, those that are connected to a triazine ring are in many cases preferred because they more fully meet the criteria mentioned above.

Although the compounds of the prior art are, in general, effective light stabilizers for synthetic organic polymers, none of them completely satisfy the stabilization requirements of polymers in their wide variety of forms and application. This is particularly true for those polymeric materials that are used in thin articles, such as fibers and films. Because of these deficiencies, there remains a need for new substances which meet the requirements more fully.

The present invention discloses the stabilization of synthetic polymers by the incorporation of an effective amount of novel triazine compounds which possess the polyalkylpiperidine moiety. The triazine-based HALS may be one selected from those described by formula (I):

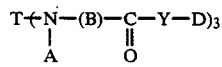
I where T is the trivalent triazine radical (II):

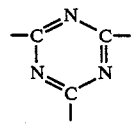
II

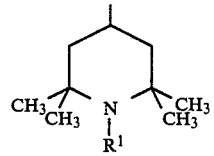

A is the hindered piperidino moiety wherein $R^1$ is independently selected from hydrogen, oxyl, hydroxyl, a straight or branched chain methylene-linked alkyl group of 1-18 carbon atoms such as methyl, ethyl, octyl, octadecyl, or 2-ethylhexyl, an alkanoyl group having 2-18 carbon atoms such as acetyl, propanoyl, butanoyl, isopentanoyl, or stearoyl, an alkenyl group of 3-4 carbon atoms, an alkenoyl group of 3-6 carbon atoms such as acryloyl, methacryloyl, crotonyl, an alkynyl group of 3-6 carbon atoms such as propargyl or 2-butynyl, a cyanomethyl group, a 2,3-epoxypropyl group, benzyl, alkylbenzyl group of 7-15 carbon atoms, or 3,5-di-tert-butyl-4-hydroxybenzyl, 3-tert-butyl-4-hydroxybenzyl or 3-tert-butyl-4-hydroxy-5-methylbenzyl, a group $—CH_2—CH(OR^2)—^3$, and a group of the formula $-(CH_2)_m—C(O)—Z$ where Z is a group selected from $-O—^4$ and $—N(R^5)(R^6)$ when m is 1 or 1 and when m is 1, Z can be a group $—C(O)—OR^7$, $R^2$ is selected from hydrogen, an aliphatic group of 1-18 carbon atoms, an araliphatic group such as benzyl and phenethyl, and an alkanoyl group having 2-18 carbon atoms, $R^3$ is selected from hydrogen, an alkyl group of 1-16 carbon atoms and phenyl, $R^4$ is selected from an alkyl group of 1-18 carbon atoms, a cycloalkyl group of 5-12 carbon atoms such as cyclopentyl, cyclohexyl, cyclooctyl, cyclododecyl, allyl, benzyl, phenyl, and a group of formula A wherein $R^1$ is described above, $R^5$ and $R^6$, same or different, are selected from hydrogen, an alkyl group having 1-8 carbon atoms such as methyl, ethyl, hexyl, a cycloalkyl group having 5-12 carbon atoms, aryl groups having 6-10 carbon atoms such as 4-methylphenyl, 2-methylphenyl, 4-butylphenyl, and aralkyl groups having 7-15 carbon atoms such as benzyl, o,m,p-alkylsubstituted benzyl, and phenethyl. In addition, $R^5$ and $R^6$, together with the N-atom to which they are attached can form a 5-7 membered ring such as pyrrolidine, piperidine and homopiperidine, $R^7$ is selected from an alkyl group of 1-18 carbon atoms, phenyl or benzyl, and is preferably methyl or ethyl, B is an alkylene group having 1-10 carbon atoms, Y is selected from $—O—$, $—NH—$ and $—NR^8—$ where $R^8$ represents an alkyl group of 1-20 carbon atoms or the group D, and D is the group

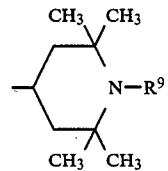

where $R^9$ is oxyl, hydroxyl, hydrogen, an alkyl group of 1-18 carbon atoms such as methyl, ethyl, etc., an alkenyl group of 3-4 carbon atoms or an alkynyl group of 3-6 carbon atoms such as propargyl.

The compounds of formula (I) can be prepared by the reaction of a substituted triazine of the formula

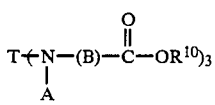

where $R^{10}$ is lower alkyl with the appropriately substituted alcohol DOH or amine D—$NH_2$ where D is the hindered amine moiety above. The reaction is generally carried out in the presence of a solvent such as ligroine or xylene, or any other solvent suitable for the reaction to occur, at or near the reflux temperature of the solvent. The reaction is best carried out using a catalyst such as lithium amide or titanium tetraisopropoxide as well as others suitable for the reaction to occur. The products of this invention may be isolated from the solvent solution and are generally purified by crystallization, trituration or any other suitable method.

An alternative means to obtain the compounds of formula (I) is to react compounds of the formula

A—NH—(B)—CO—Y—D with cyanuric chloride in a solvent such as dioxane, toluene or any other solvent so long as it does not interfere with the reaction, at or near the reflux temperature of the solvent, in the presence of a base such as carbonate, hydroxide, and the like, for the removal of the generated hydrogen chloride.

Some of these starting compounds and the means for their preparation have been described in U.S. Pat. Nos. 4,578,472 and 4,670,488. These compounds may be prepared in a two-step process by the reaction of compound A—$NH_2$ with a halogenated carboxylic acid or ester represented by the formula

X—(B)—COO—$^{11}$, wherein X represents the halogen atom, and $R^{11}$ represents a hydrogen atom or lower alkyl group.

The second step of the sequence involves transesterifying or amidating the compound produced from the first step with the desired alcohol or amine either in the presence of a solvent or neat, in the presence of a catalyst as known in the art. Examples of appropriate solvents without introducing any limitations are ligroine, xylene, toluene, etc. or a mixture thereof. Examples of suitable catalysts are, without introducing any limitations, lithium amide and titanium tetraisopropoxide.

The reaction will generally be carried out at or near the reflux temperature of the solvent when one is used, otherwise the temperature is between 100 and 200° C. The product of the reaction can usually be isolated by partitioning the reaction mixture between water and the solvent of the reaction and subsequent removal of the solvent. The products can be purified by recrystallization or any other suitable method.

The 4-aminopolyalkylpiperidines used as intermediates for conversion to compounds of the invention are known from U.S. Pat. No. 3,684,765 and in general are prepared by the reductive amination of the corresponding ketone using either ammonia or the amine of interest.

In the examples of the invention where $R^1$ is other than hydrogen, the additional derivatization can be carried out either on compounds of the formulas:

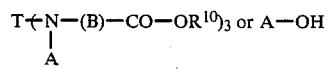 or A—OH so long as the transformation does not destroy the integrity of the product. An alternative manner to perform the substitution especially for compounds where Y is to be

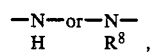

is to derivatize corresponding derivatives of 4-oxopiperidine and then introduce the 4-amino substituent by reductive amination.

The reductive amination can be carried out in the manner that has been well described in the prior art and primary literature. In general, any catalyst that is commonly used in catalytic hydrogenation reactions can be used. Preferred catalysts include palladium on carbon and platinum on carbon. The reaction is normally run in the presence of a solvent. Suitable solvents without including any limitations include methanol and ethanol. The hydrogenation is usually carried out at a hydrogen pressure of 1-10 atmospheres and at a temperature necessary to achieve the reduction. In general, the reduction can be achieved at ambient temperature but in some instances up to about 100° C. may be used.

The introduction of an alkyl, alkenyl, alkynyl, aralkyl, and 2,3-epoxy-propyl group can be achieved by reaction of the initially prepared 4-oxopiperidine or the derivatized triazine which contain the free N—H of the piperidine with the suitable halide. Examples of suitable halides include methyl iodide, methyl chloride, ethyl bromide, dodecyl chloride, octadecyl chloride, allyl bromide, methallyl chloride, butenyl chloride, propargyl chloride, benzyl chloride, phenethyl bromide, and epichlorohydrin. The generated hydrogen halide can be scavenged by the addition of an inorganic base such as carbonate or hydroxide or by the addition of an organic amine such as triethylamine to the reaction mixture.

The introduction of an alkanoyl or an alkenoyl group can be performed by acylation of the N—H group using the suitable acid halide or, when convenient, the acid anhydride. If the acid halide is used, the generated hydrogen halide can be scavenged in the same manner as stated previously. Examples of such groups are acetyl chloride, acetic anhydride, propionic anhydride, hexanoyl chloride, dodecanoyl chloride, and octadecanoyl chloride.

For the introduction of the group —$CH_2$—CH—(O—$R^2$)—$R^3$ the substituent can be introduced by reaction of the parent N—H compound with the corresponding alkylene oxide such as ethylene oxide, propylene oxide and styrene oxide. The resulting hydroxy compound can be acylated in the manner commonly known in the art using the suitable acid halide and can be alkylated by formation of the alkoxide and reaction with the desired alkyl halide.

When $R^1$ is the group —$(CH_2)_m$—C(O)—Z and m is zero the appropriate group can be attached by reacting the parent N—H compound with a chloroformate such as methyl chloroformate, ethyl chloroformate, allyl chloroformate, hexyl chloroformate, decyl chloroformate, octadecyl chloroformate, and phenyl chloroformate. The preparation of the oxamide half esters can be achieved by the reaction of the N—H compound with the oxalyl chloride monoalkyl ester such as oxalyl chloride monoethyl ester and scavenging the generated hydrogen chloride as stated previously. When $R^1$ is the group —$(CH_2)_m$—$C(O)$—Z and m is 1, the appropriate group can be attached by reacting the parent N—H compound with the appropriate ester of chloroacetic acid such as methyl chloroacetate, ethyl chloroacetate, allyl chloroacetate, phenyl chloroacetate, and cyclohexyl chloroacetate.

The preparation of the corresponding ureas can be achieved by treating the parent N—H compound with the suitable carbamyl halide such as methyl carbamyl chloride, ethyl carbamyl chloride, dimethyl carbamyl chloride, phenyl carbamyl chloride, pyrrolidine carbamyl chloride, and piperidine carbmayl chloride. Alternatively the ureas can be prepared by treating the parent N—H compound with the suitable isocyanate.

For $R^1$ as the oxyl group or hydroxyl group the parent N—H compound can be treated with an oxidizing agent such as hydrogen peroxide in the presence of a catalyst like sodium tungstate or with a percarboxylic acid, like metachloroperbenzoic acid, with subsequent reduction of the oxyl by catalytic hydrogenation if the hydroxyl is desired.

The compounds of this invention are effective light stabilizers for synthetic organic polymers. The following nonlimiting examples are offered to demonstrate the invention:

2,4,6-tris-[N-(2,2,6,6-tetramethyl-4-piperidyl)aminoacetic acid]-1,3,5-triazine, tris ester with 2,2,6,6-tetramethyl-4-piperidinol, 2,4,6-tris-[N-(2,2,6,6-tetramethyl-4-piperidyl)aminoacetic acid]-1,3,5-triazine, tris ester with 1,2,2,6,6-pentamethyl-4-piperidinol, 2,4,6-tris-[N-(2,2,6,6-tetramethyl-4-piperidyl)aminoacetic acid]-1,3,5-triazine, tris amide with 4-amino-2,2,6,6-tetramethylpiperidine, 2,4,6-tris-(3-[N-(2,2,6,6-tetramethyl-4-piperidyl)aminopropionic acid])-1,3,5-triazine, tris ester with 2,2,6,6-tetramethyl-4-piperidinol, 2,4,6-tris-(3-[N—1,2,2,6,6-pentametyl-4-piperidyl)aminopropionic acid-])1,3,5-triazine, tris ester with 1,2,2,6,6-pentamethyl-4-piperidinol, 2,4,6-tris-[N-(1-acetyl-2,2,6,6-tetramethyl-4-piperidyl)aminoacetic acid]-1,3,5-triazine, tris ester with 1-acetyl-2,2,6,6-tetramethyl-4-piperidinol, 2,4,6-tris-[N-(1,2,2,6,6-pentamethyl-4-piperidyl)aminoacetic acid]-1,3,5-triazine, tris ester with 2,2,6,6-tetramethyl-4-piperidinol, 2,4,6-tris-(4-[N-(2,2,6,6-tetramethyl-4-piperidyl)aminobutanoic acid])-1,3,5-triazine, tris ester with 2,2,6,6-tetramethyl4-piperidinol, 2,4,6-tris-(11-[N-(2,2,6,6-tetramethyl-4-piperidyl)aminoundecanoic acid])-1,3,5-triazine, tris ester with 2,2,6,6-tetramethyl-4-piperidinol, 2,4,6-tris-(3-[N-(2,2,6,6-tetramethyl-4-piperidyl)amino-2-methylpropionic acid])-1,3,5-triazine, tris ester with 2,2,6,6-tetramethyl-4-piperidinol, and 2,4,6-tris-(6-[N-(2,2,6,6-tetramethyl-4-piperidyl)aminohexanoic acid])-1,3,5-triazine, tris ester with 2,2,6,6-tetramethyl-4-piperidinol.

The compounds of this invention are effective light stabilizers for synthetic organic polymers. In addition to their effective light stabilizing properties, some of the compoounds of this invention also exhibit excellent thermal stabilizing performance. Among the synthetic organic polymers which can be stabilized by the compounds of this invention are the polyolefins which include homopolymers of olefins like polyethylene, both high- and low-density polyethylene, polypropylene, polybutadiene, polystyrene, and the like; and copolymers of olefins with other ethylenically unsaturated monomers such as ethylene-propylene copolymer, ethylenebutylene copolymer, ethylene-vinyl acetate copolymer, styrene-butadiene copolymer and the like; terpolymers such as acrylonitrilebutadiene-styrene and the like; polyvinyl chlorides, polyvinylidene chlorides, copolymers of vinyl chloride and vinylidene chloride with vinyl acetate or other ethylenically unsaturated monomer; polyacetals such as polyoxymethylene and polyoxyethylene; polyesters such as polyethylene terephthalate; polyamides such as polyamide 6, polyamide 6,6, polyamide 6,10; polyurethanes and polymers derived from -unsaturated acids and derivatives thereof; polycarbonates; polyacrylates and polymethacrylates, polyacrylic amides and polyacrylonitrile, as well as copolymers of acrylic acid and one or more of its derivatives with a melamineformaldehyde resin.

Of particular importance among these groups of polymers is the stabilization of polyolefins. The compounds of this invention are excellent for their stabilization. Generally the stabilizers of the invention are added to the polymer to be stabilized in an amount ranging from 0.01 to 5.0% by weight based on the weight of the polymer to be stabilized. Preferably they may be used in an amount between 0.05 and 1% by weight.

The compounds of the invention may also be used in conjunction with other stabilizers for the preparation of stabilized compositions. Among these other additives may be antioxidants, supplemental light stabilizers such as UV absorbers or other hindered amines, metal deactivators, etc., pigments, colorants, fillers, flame retardants, antistatic agents, and the like.

Suitable antioxidants include those of the hindered phenol type such as 2,6-di-t-butyl-p-cresol; 2,4,6-tri-t-butylphenol; 2,2'-thiobis(4-methyl-6-t-butylphenol); octadecyl-3-(3',5'-di-t-butyl-4'-hydroxyphenol)propionate; pentaerythrityl tetrakis (3',5'-di-t-butyl-4-hydroxyphenyl) propionate; 1,3,5-tris(3',5'-di-t-butyl-4'-hydroxybenzyl) isocyanurate; 1,3,5-tris(2,6-dimethyl-4-t-butyl-3-hydroxybenzyl) isocyanurate; 3,5-di-t-butyl-4-ydroxy hydrocinnamic acid triester with 1,3,5-tris(2-hydroxyethyl)-s-triazine-2,4,6-(1H,3H,5H) trione;

Esters of thiodipropionic acid such as dilaurylthiodipropionate and distearylthiodipropionate are also included.

Phosphites such as triphenyl phosphite, trinonylphenyl phosphite, distearyl pentaerythrityl diphosphite, diphenyldecyl phosphite, tris-(2,4-di-t-butylphenyl)-phosphite, bis(2,4-di-t-butylphenyl)pentaerythritol diphosphite can be used.

Supplemental light stabilizers such as those of the benzotriazole class including 2-(2'-hydroxy-5'-t-octylphenyl)benzotriazole; 2-(2'-hydroxy-3',5'-di-t-butylphenyl)-5-chlorobenzotriazole; 2-(2'-hydroxy-5'-methylphenyl) benzotriazole; 2-(2'-hydroxy-3'-t-butyl-5'-methylphenyl)benzotriazole; 2-(2'-hydroxy-3',5'-di-t-amylphenyl)benzotriazole; those of the hydroxybenzophenone type such as 2-hydroxy-4-methoxybenzophenone; 2-hydroxy-4-octyloxybenzophenone; 2,2'-dihydroxy-4,4'-dimethoxybenzophenone;

Esters of hindered phenols such as n-hexadecyl-3,5-di-t-butyl-4-hydroxybenzoate and 2',4'-di-t-butylphenyl 3,5-di-t-butyl-4-hydroxybenzoate;

Metal complexes such as nickel complexes of 2,2'-thiobis-(4-tert-octylphenol), nickel dibutyl dithiocarbamate; nickel salts of 3,5-di-t-butyl 4-hydroxybenzylphosphonic acid monoalkyl esters where alkyl is methyl, ethyl, propyl and butyl, and nickel complexes of 2-hydroxy-4-methylphenylundecylketoneoxime.

Other examples of suitable supplemental light stabilizers may be found in U.S. Pat. Nos. 3,488,290 and 3,496,134.

The following unlimiting preparative examples are given to illustrate the invention wherein all expressed proportions are by weight unless otherwise specified.

EXAMPLE 1

Preparation of 2,4,6-tris-[N-(2,2,6,6-tetramethyl-4-piperidylamino)acetic acid]-1,3,5-triazine, tris ester with 2,2,6,6-tetramethyl-4-piperidinol.

A mixture of N-(2,2,6,6-tetramethyl-4-piperidylamino)acetic acid, ester with 2,2,6,6-tetramethyl4-piperidinol (4.67g, 13.2 mmol) and cyanuric chloride (0.82g, 4.4 mmol) was combined in dioxane (30 mL). Powdered potassium carbonate (1.82g, 13.2 mmol) was added and the mixture was heated to reflux for 18 hrs. Upon completion of the reaction, the dioxane was removed, the residue was taken up in methylene chloride and washed with water. After drying and concentrating, the product was obtained as a white solid. Recrystallization from ligroine yielded 3.5g (70%) of the product having a melting point of 170°–172° C.

EXAMPLE 2

Preparation of 2,4,6-tris-[N-(2,2,6,6-tetramethyl-4-piperidylamine)acetic acid]-1,3,5-triazine, tris ester with 1,2,2,6,6-pentamethyl-4-piperidinol.

This compound was prepared in a manner identical to the procedure used for the preparation of Example 1. The product was obtained as a white solid having a melting point of 145°–154° C.

EXAMPLE 3

Preparation of 2,4,6-tris-[N-(2,2,6,6-tetramethyl-4-piperidylamino)acetic acid]-1,3,5-triazine, tris amide with 4-amino-2,2,6,6-tetramethylpiperidine.

This compound was prepared in a manner identical to the procedure used for the preparation of Example 1. The product was obtained as a white solid after manipulation having a melting point of 121°–136° C.

EXAMPLE 4

Preparation of 2,4,6-tris-(3-(N-(2,2,6,6-tetramethyl-4-piperidylamino)propionic acid)), tris ester with 2,2,6,6-tetramethyl-4-piperidinol.

This compound was prepared in a manner identical to the procedure used for the preparation of Example 1. The product was obtained as a white solid having a melting point of 84–86° C.

EXAMPLE

Preparation of 2,4,6-tris-(6-(N-(2,2,6,6-tetramethyl-4-piperidylamino)hexanoic acid, tris ester with 2,2,6,6-tetramethyl-4-piperidinol.

This compound may be prepared in a manner nearly identical to the procedure used for the preparation of EXAMPLE 1.

EXAMPLES 6–10

In order to further illustrate the effectiveness of the above-described compounds as light stabilizers, the materials described by Examples 1–4 were each incorporated into a commercially available polypropylene resin manufactured by Hercules Corporation as Pro-Fax 6301 Polypropylene Resin. The light stabilizers were incorporated into the polypropylene by solvent blending (methylene chloride) at a concentration of 0.25% by weight of the total resin composition. A primary antioxidant (stearyl beta( 3,5-di-t-butyl-4-hydroxyphenylpropionate)) was used at a level of 0.2%. The resin was then extruded at 200° C. and compression molded at 6,000 psi at 188° C. to produce films having a thickness of 5 mils. A control film was also produced by an identical procedure with the light stabilizer omitted. Each film was exposed to a Xenon Arc in an Atlas Weather-o-Meter until the IR carbonyl increase by 0.5, which is considered to be the failure point.

EXAMPLES 11–15

In order to illustrate the effectiveness of the above compounds for thermal stabilization, the plaques prepared in the same manner as above were placed in a forced draft oven at 150° C. Failure was determined when the first signs of decomposition were observed, as evidenced by crumpling and/or flaking of the plaque. Tests were run in quadruplicate and an average value was determined. Results are listed in Table 2.

TABLE 1

| Example # | Stabilizer | Hrs to Failure |
|---|---|---|
| 6 | Control | 400 |
| 7 | Compound 1 | >9000 |
| 8 | Compound 2 | >4000 |
| 9 | Compound 3 | >4000 |
| 10 | Compound 4 | >4000 |

TABLE 2

| Example # | Stabilizer | Hrs to Failure |
|---|---|---|
| 11 | Control | 120 |
| 12 | Compound 1 | 455 |
| 13 | Compound 2 | 288 |
| 14 | Compound 3 | 300 |
| 15 | Compound 4 | 216 |

What is claimed is:

1. A compound of the formula $$T(\!-\!N\!-\!(B)\!-\!\overset{O}{\underset{\|}{C}}\!-\!Y\!-\!D)_3 \qquad \qquad I$$
$$\phantom{T(\!-\!N\!-\!}|\phantom{(B)\!-\!C\!-\!Y\!-\!D)_3}$$
$$\phantom{T(\!-\!N\!-\!}A$$

where T is the trivalent triazine radical $$-\overset{}{\underset{}{C}}\overset{N}{\underset{N}{\overset{\|}{\diagdown}}}\overset{}{\underset{C}{\overset{\|}{C}}}- \qquad \qquad II$$

and where A is the hindered piperidino moiety

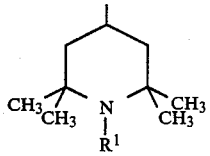

wherein R¹ is selected from the group consisting of hydrogen, oxyl, hydroxyl, a straight or branched chain methylene-linked alkyl group of 1-18 carbon atoms, an alkanoyl group having 2-18 carbon atoms, an alkenyl group of 3-4 carbon atoms, an alkenyl group of 3-6 carbon atoms, an alkynyl group of 3-6 carbon atoms, a cyanomethyl group, a 2,3-epoxypropyl group, a benzyl or alkylbenzyl group of 7-15 carbon atoms, a group —CH₂CH(OR²)—³ and a group of the formula —CH₂CH(OR²)$_m$—C(O)—Z wherein Z is a group selected from —OR⁴ and —N(R⁵)(R⁶) when m is 1 or 0 and when m is 0, Z can be a group —C(O)—OR⁷, R² is selected from the group consisting of hydrogen, an aliphatic group of 1-18 carbon atoms, an araliphatic group and an alkanoyl group, R³ is selected from the group consisting of hydrogen, an alkyl group of 1-16 carbon atoms and phenyl, R⁴ is selected from the group consisting of an alkyl group of 1-18 carbon atoms, a cycloalkyl group of 5-12 carbon atoms, allyl, benzyl, phenyl, and a group of formula A, R⁵ and R⁶, same or different, are selected from the group consisting of hydrogen, an alkyl group having 1-8 carbon atoms, a cycloalkyl group having 5-12 carbon atoms, an aryl group having 6-10 carbon atoms, an aralkyl group having 7-15 carbon atoms, and additionally R⁵ and R⁶, together with the N-atom to which they are attached, can form a 5-7 membered ring consisting of pyrrolidine, piperidine, and homopiperidine, R⁷ is selected from the group consisting of an alkyl group of 1-18 carbon atoms, phenyl and benzyl, B is an alkylene group having 1-10 carbon atoms, Y is selected from the group consisting of —O—, —NH—, and —N(R⁸)- where R⁸ represents an alkyl group of 1-20 carbon atoms or the group D, and D is the group

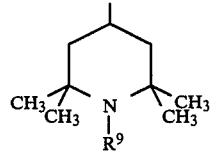

where R⁹ is oxyl, hydroxyl, hydrogen, an alkyl group of 1-18 carbon atoms, an alkenyl group of 3-4 carbon atoms or an alkynyl group of 3-4 carbon atoms.

2. A compound of claim 1 wherein R¹ is selected from the group consisting of hydrogen, methyl and acetyl, and Y is —O— and —NH—.

3. A compound of claim 2 wherein B is selected from methylene, ethylene and hexylene.

4. A compound of claim 3 wherein R¹ and R⁹ are hydrogen, Y is —O— and B is methylene.

5. A compound of claim 3 wherein R¹ is hydrogen, R⁹ is methyl, Y is —O— and B is methylene.

6. A compound of claim 3 wherein R and R⁹ are hydrogen, Y is —O— and B is ethylene.

7. A compound of claim 3 wherein R¹ and R⁹ are hydrogen, Y is —NH— and B is methylene.

8. A compound of claim 3 wherein R¹ and R⁹ are hydrogen, Y is —O— and B is hexylene.

9. A synthetic polymer composition stabilized against light-induced degradation comprising an organic polymer normally subjected to deterioration by light containing from 0.01-5% by weight of a compound of claim 1.

10. A composition of claim 9 wherein the organic polymer is a polyolefin homopolymer or copolymer.

11. A composition of claim 10 wherein said organic polymer is a homo- or copolymer of propylene.

* * * * *

UNITED STATES PATENT AND TRADEMARK OFFICE
CERTIFICATE OF CORRECTION

PATENT NO. : 4,883,860

DATED : November 28, 1989

INVENTOR(S) : Richard V. Nelson and John F. Stephen

It is certified that error appears in the above-identified patent and that said Letters Patent is hereby corrected as shown below:

Column 2, line 24, "$-CH_2-CH(OR^2)-^3$" should read ---$CH_2-CH(OR^2)-R^3$--.

Column 2, line 26, "$-O-^4$" should read ---$O-R^4$--.

Col. 2, lines 26, 27, "when m is 1 or 1 and when m is 1," should read --when m is 1 or 0 and when m is 0,--.

Column 3, line 40, "$X-(B)-COO-^{11}$," should read --$X-(B)-COO-R^{11}$,--.

Column 5, line 66, "compoounds" should read --compounds--.

UNITED STATES PATENT AND TRADEMARK OFFICE
CERTIFICATE OF CORRECTION

PATENT NO. : 4,883,860

DATED : November 28, 1989

INVENTOR(S) : Richard V. Nelson and John F. Stephen

It is certified that error appears in the above-identified patent and that said Letters Patent is hereby corrected as shown below:

In The Claims:

Column 9, line 18, "$-CH_2CH(OR^2)-^3$" should read ---$CH_2CH(OR^2)-R^3$---.

Column 9, line 20, "$-CH_2CH(OR^2)m-C(O)-Z$" should read ---$(CH_2)m-C(O)-Z$---.

Signed and Sealed this

Sixteenth Day of July, 1991

*Attest:*

HARRY F. MANBECK, JR.

*Attesting Officer*     *Commissioner of Patents and Trademarks*